US008163872B2

(12) United States Patent
Aassveen et al.

(10) Patent No.: US 8,163,872 B2
(45) Date of Patent: Apr. 24, 2012

(54) PURIFICATION OF GLYCOPEPTIDES

(75) Inventors: Lene Aassveen, Oslo (NO); Kamilla Lundhaug, Oslo (NO); Kjersti Aastorp Hirth, Oslo (NO)

(73) Assignee: Xellia Pharmaceuticals APS (DK)

( * ) Notice: Subject to any disclaimer, the term of this patent is extended or adjusted under 35 U.S.C. 154(b) by 728 days.

(21) Appl. No.: 11/577,916

(22) PCT Filed: Oct. 27, 2005

(86) PCT No.: PCT/EP2005/011631
§ 371 (c)(1),
(2), (4) Date: Jul. 13, 2009

(87) PCT Pub. No.: WO2006/045627
PCT Pub. Date: May 4, 2006

(65) Prior Publication Data
US 2009/0275739 A1    Nov. 5, 2009

(30) Foreign Application Priority Data

Oct. 27, 2004  (DK) ................................ 2004 01652
Nov. 15, 2004  (DK) ................................ 2004 01768

(51) Int. Cl.
*C07K 1/18*  (2006.01)
*C07K 1/30*  (2006.01)
*C07K 9/00*  (2006.01)
(52) U.S. Cl. ....................................... 530/322; 530/344
(58) Field of Classification Search .................. None
See application file for complete search history.

(56) References Cited

U.S. PATENT DOCUMENTS

| 4,440,753 | A |   | 4/1984 | McCormick et al. |
| 5,223,413 | A | * | 6/1993 | Nagy et al. ................ 435/71.3 |
| 5,235,037 | A |   | 8/1993 | Krishnan |
| 2004/0024177 | A1 |   | 2/2004 | Kang et al. |

FOREIGN PATENT DOCUMENTS

| EP | 0437846 | 7/1991 |
| EP | 0479086 | 4/1992 |
| HU | 0213228 B1 | 7/1997 |

OTHER PUBLICATIONS

International Preliminary Report on Patentability; International Application No. PCT/EP2005/011631; International Filing Date Oct. 27, 2005; Applicant's File Reference APWO05520; Date of Issuance May 1, 2007; 6 pages.
International Search Report; International Application No. PCT/EP2005/011631; International Filing Date Oct. 27, 2005; Applicant's File Reference APWO05520; Date of Mailing Mar. 29, 2006; 11 pages.
Argonaut Technologies 2002—Product Sheets; "Method Development in Solid Phase Extraction Using ISOLUTE SCX-2 SPE Columns for the Extraction of Aqueous Samples"; Corporate Headquarters, 1100 Chess Drive, Foster City, CA 94404, (605) 655-4200)); (2002); 5 pages.
GE Healthcare—Instructions 71/7149-00 AN, HiTrap ion exchange cols.; "HiTrap SP HP, 1ml and 5ml HiTrap Q HP, 1 ml and 5ml"; www.gehealthcare.com/hitrap; 20 pages; (2006).
"Ion Exchange Chromatography"; Principles and Methods, Amersham Biosciences; pp. 1-162; (1999).
Kennedy et al.; Multimodal Liquid Chromatography Columns for the Separation of Proteins in Either and Anion-Exchange or Hydrophobic-Interaction Mode; J. Chromatogr. 359; pp. 73-84; (1986).
Letter dated Oct. 19, 2011 from Marshall, Gerstein & Borun LLP; 4 pages.
Nagarajan; "Glycopeptide Antibiotics"; Marcel Dekker, Inc.; pp. 31-32; (1994).
Pefferkorn; "Interfacial Phenomena in Chromatography"; Marcel Dekker, Inc.; p. 287; (1999).
Takacs-Noval et al.; "Acid-base Properties and Proton-speciation of Vancomycin"; Int. J. Pharm.; 89; pp. 261-263; (1993).
Weston et al.; "2.4 Hydrophobic-Interaction Chromatography"; in HPLC and CE: Principles and Practices; W.B. Saunders Co.; p. 38; (1997).

* cited by examiner

*Primary Examiner* — Jeffrey E Russel
(74) *Attorney, Agent, or Firm* — Cantor Colburn LLP

(57) ABSTRACT

A novel and improved method for purification of glycopeptides, especially glycopeptide antibiotics. The method comprises contacting a solution of the glycopeptide to an ion exchange chromatography material. The product of this method has a surprisingly high purity.

19 Claims, No Drawings

US 8,163,872 B2

PURIFICATION OF GLYCOPEPTIDES

The present invention is related to a novel and improved method for purification of glycopeptides, especially glycopeptide antibiotics. The method comprises contacting a solution of the glycopeptide to an ion exchange chromatography material. The product of this method has a surprisingly high purity.

BACKGROUND OF THE INVENTION

Glycopeptide antibiotics can be classified in four groups based on their chemical structure (according to Yao, R. C. and Crandall, L. W., Glycopeptides, Classification, Occurrence, and Discovery in Glycopeptide antibiotics, ed. Nagarajan, R., Marcel Dekker, Inc., N.Y, N.Y., Chapter 1, pp. 1-27 (1994)):
  Group I (or the vancomycin type) has aliphatic amino acids at positions 1 and 3;
  Group II (or the avoparcin type) has aromatic amino acid residues at positions 1 and 3;
  Group III (or the ristocetin type) is similar to group II but for an ether linkage joining the aromatic amino acids at positions 1 and 3; and
  Group IV (or the Teicoplanin type) has the same amino acid arrangement as group III plus a fatty acid residue attached to the amino sugar.

Examples on glycopeptide antibiotics are listed in U.S. Pat. No. 4,845,194 A, and in EP 836 619 B1, wherein the term dalbaheptide is used for glycopeptide antibiotics. The glycopeptides can be manufactured as disclosed in the art, such as by fermentation.

Teicoplanin is a glycopeptide antibiotic produced by *Actinoplanes teichomyceticus* and was discovered during a scientific research program aiming to find new molecules of microbial origin that inhibited bacterial cell wall synthesis. (Goldstein, B. et al, Teicoplanin in Glycopeptide Antibiotics, ed. Nagarajan, R., Marcel Dekker, Inc., N.Y, N.Y., Chapter 8, pp. 273-307 (1994)). It was first described in 1978 and ten years later it was introduced into clinical practice in Italy. (Parenti, F. et al, J. Chemotherapy, Vol. 12, pp. 5-14, (2000)).

Numerous methods for purifying glycopeptide antibiotics have been disclosed. According to the method disclosed in EP 479 086 B1, in order to increase extraction efficiency of teicoplanin A2, the fermentation broth is adjusted to a pH between 10 and 11.5, prior to filtration. The filtrate of the fermentation broth is loaded on a polyamide resin and teicoplanin is precipitated from the eluate with an excessive amount of acetone and left to stand for 3 hours. The supernatant is decanted and the rest is filtered. The resulting cake is washed with acetone to recover teicoplanin A2. This method has the problem of solvent accumulation, since it uses an excessive amount of acetone in diverse steps.

U.S. Pat. No. 4,845,194 discloses a method for recovering vancomycin-type glycopeptide antibiotics (e.g. teicoplanin and vancomycin), in which a cation exchange resin having a cross-linkage of 2% or less is added to the fermentation broth to adsorb teicoplanin to the resin and a 100 mesh sieve is used to separate the mycelia from the resin. Then, the resin is washed with purified water, followed by elution to recover teicoplanin.

Korean Patent Publication No. 2000-0066479 discloses a method for producing teicoplanin A2, in which a fermentation broth is adjusted to pH 11 and centrifuged, and the supernatant is adsorbed onto a synthetic adsorbent resin such as XAD-16, HP-20 and activated carbon or silica gel, eluted with a 50 to 80% methanol solution and recovered under reduced pressure to obtain teicoplanin as crude powder. The crude teicoplanin is dissolved in a solution of sodium acetate and purified by sugar affinity chromatography.

US patent application 20040024177 A1 discloses method for purifying teicoplanin A2 comprising: (i) a primary pre-purification step of purifying a filtrate of fermentation broth of a strain using a synthetic adsorbent; (ii) a secondary pre-purification step of purifying the primary pre-purification solution using a cation exchange resin having a high cross-linkage, a catalytic resin or a chelate resin; (iii) a final purification step of purifying the secondary pre-purification solution using a reversed phase resin; and (iv) a powder-forming step.

SUMMARY OF THE INVENTION

There still remains a need for a method that can be used to mass produce glycopeptide antibiotics with high purity. According to the present invention, it is possible to obtain glycopeptide antibiotics with high purity through a novel method for ion exchange chromatography.

The present inventors have surprisingly found out that it is possible to obtain a glycopeptide, especially a glycopeptide antibiotic, in high purity by using a method comprising ion exchange chromatography of the glycopeptide containing solution with increased salt concentration and/or increased conductivity of the solution. Not wishing to be bound by theory, it is contemplated that this method can be used for purification of all glycopeptides that share a common structure, i.e. the dalbaheptide structure.

In accordance with this finding, there is provided a method for purification of a glycopeptide, especially a glycopeptide of dalbaheptide type using ion exchange chromatography, which method comprises raising the salt concentration in a solution of the glycopeptide (and thereby raising the conductivity of the solution) to a level higher that hitherto disclosed, while the glucopeptide is allowed to bind to an ion exchange resin.

DESCRIPTION OF THE INVENTION

The present invention relates to a method for purification of a glycopeptide antibiotic or a derivative thereof (or a solution comprising the glycopeptide antibiotic or the derivative thereof), which comprises:
a) adjusting the salt concentration in a solution of the glycopeptide to at least 0.2 M, and/or adjusting the conductivity of the solution of the glycopeptide to at least 20 mS/cm;
b) contacting the solution of the glycopeptide with an ion exchange material;
c) optionally washing the ion exchange material; and
d) removing the glycopeptide from the ion exchange material, using an eluent.

Preferably, the glycopeptide antibiotic is an oligopeptide (e.g. heptapeptide) antibiotic, characterized by a multi-ring peptide core optionally substituted with saccharide groups, such as an antibiotic selected from the group consisting of: a dalbaheptide, a glycopeptide of group I (vancomycin type); a glycopeptide of group II (avoparcin type); a glycopeptide of group III (ristocetin type); a glycopeptide of group IV (teicoplanin type); derivatives of any of these; individual factors of any of these; and combinations thereof. Examples of glycopeptides included in this definition may be found in "Glycopeptides Classification, Occurrence, and Discovery", by Raymond C. Rao and Louise W. Crandall, ("Drugs and the Pharmaceutical Sciences" Volume 63, edited by Ramakrishnan Nagarajan, published by Marcal Dekker, Inc.). Additional examples of glycopeptides are disclosed in U.S. Pat.

Nos. 4,639,433; 4,643,987; 4,497,802; 4,698,327; 5,591,714; 5,840,684; and 5,843.889; in EP 0 802 199; EP 0 801 075; EP 0 667 353; WO 97/28812; WO 97/38702; WO 98/52589; WO 98/52592; and in J. Amer. Chem. Soc., 1996, 118, 13107-13108; J. Amer. Chem. Soc, 1997, 119, 12041-12047; and J. Amer. Chem. Soc, 1994, 116, 4573-4590. Representative glycopeptides include those identified as A477, A35512, A40926, A41030, A42867, A47934, A80407, A82846, A83850, A84575, AB-65, Actaplanin, Actinoidin, Ardacin, Avoparcin, Azureomycin, Balhimycin, Chloroorientien, Chloropolysporin, Decaplanin, N-demethylvancomycin, Eremomycin, Galacardin, Helvecardin, Izupeptin, Kibdelin, LL-AM374, Mannopeptin, MM45289, MM47756, MM47761, MM49721, MM47766, MM55260, MM55266, MM55270, MM56597, MM56598, OA-7653, Orenticin, Parvodicin, Ristocetin, Ristomycin, Synmonicin, Teicoplanin, UK-68597, UK-69542, UK-72051, Vancomycin, and the like, and derivatives of any of these. The presently most interesting glycopeptide antibiotic to be purified is the teicoplanin complex (including the A2 factor), which results from a fermentation broth.

More preferably the glycopeptide is selected from the group consisting of: A40926, A84575, Ardacin, kibdelin, MM55266, Parvodicin, vancomycin, the Teicoplanin complex and its factors, and derivatives of these.

The term "derivatives" comprises glycopeptides that still comprise the cyclic peptide skeleton (e.g. the dalbaheptide skeleton), but differ from the above mentioned glycopeptides in that a substituent directly or indirectly bound to the skeleton has been removed or replaced by an other substituent. Examples on derivatives are: fully or partly deglycosylated glycopeptides, such as aglycones, and derivatives which are disclosed in the art, such as in WO 0198328 A, WO 0183521 A, WO 03018607 A, WO 03018608 A, WO 03029270 A, EP 201 251 A, US 20040087494 A1, U.S. Pat. No. 5,164,484 A, U.S. Pat. No. 5,916,873 A, and in references cited in any of these patent documents.

It is contemplated that both anion and cation exchange materials might be used, but it is presently preferred that the ion exchange material is an anion exchange resin, preferably an anion exchange resin in which the backbone has a polymeric hydrophilic nature, such as Macroprep High Q Support (BioRad).

The conductivity of the solution of the glycopeptide is above preferably above 15 mS/cm, more preferred above 20 mS/cm, above 25 mS/cm, or above 30 mS/cm. The conductivity can be above 40 mS/cm.

It is preferred that the salt concentration during the ion exchange is higher than about 0.25 M, such as higher than 0.30 M or even higher than 0.35 M or 0.45 M, and it is preferred that the salt concentration during the ion exchange is lower than about 2.0 M, such as lower than 1.5 M, tower than 1.0 M or even lower than 0.7 M. It is presently preferred that the salt concentration is in the range of 0.4 to 0.7 M. The NaCl adjustment may be performed by measuring the added salt.

Examples of salts that can be used in connection with the present invention for adjusting the salt concentration and/or the conductivity of the solution are alkali metal salts, e.g., selected from the group consisting of: Sodium, potassium or lithium salts of one of the following anions: $Cl^-$, $HSO_3^-$, $BrO_3^-$, $Br^-$, $NO_3^-$, $ClO_3^-$, $HSO_4^-$, $HCO_3^-$, $IO_3^-$, $HPO_4^{2-}$, formate, acetate, or propionate. Presently, NaCl is preferred. A mixture of different salts can be used.

Examples on eluents that can be used (especially in connection with the anion exchange resin) are:
An acid, such as an acid selected from the group consisting of:
A) a weak organic acid, preferably acetic acid or citric acid; or
B) a buffer composed of a weak organic acid and a corresponding base, preferably below pH 4.5; and
a solution of a salt, such as a salt defined above, including mixtures thereof.

It is presently preferred that the eluent is acetic acid, and/or that the concentration of the acid is higher than 0.1 M (such as higher than 0.3 M; 0.5 M; 0.8 M), and it is presently preferred that it is higher than 1.0 M. However, the concentration of the acid should be lower than 6.0 M, more preferred lower than 4.0 M. A mixture of different acids can be used. If an aqueous solution of a salt is used as eluent, the concentration of the salt should preferably be higher than 1.5 M. It is apt that the eluent is acetic acid, and/or that the concentration of the acid is from 0.1 M to 6.0 M, more preferred from 1.0 M to 4.0 M. A mixture of different acids can be used.

An embodiment of the invention relates to a method as above, which further comprises the following steps:
a) obtaining a crude fermentation broth containing a glycopeptide antibiotic producing microorganism;
b) adjusting the pH of the crude fermentation broth to between pH 8 and pH 12; and
c) separating the fermentation broth from the glycopeptide antibiotic producing microorganism (mycelial mass), e.g. by centrifugation or filtration, thereby obtaining a glycopeptide antibiotic containing solution.

It is preferred that the pH is adjusted to 9-11, and that the separation is carried out at a temperature between 0 and 25 degrees C.; more preferably at a temperature between 5 and 15 degrees C.

The method of the invention might comprise one or more purification steps for obtaining a more pure glycopeptide, such as purification steps selected from the group consisting of:
a) Reverse phase chromatography, e.g. HPLC;
b) absorbent chromatography;
c) filtration;
d) reverse osmosis;
e) decolorisation by treatment with activated carbon or an absorbent resin;
f) Cation exchange chromatography;
h) Precipitation;
i) centrifugation;
j) affinity chromatography; and
k) liquid-liquid extraction,
or for example selected from (a) to (i) above.

Solid glycopeptide can be isolated from the purified solution in a manner known to the person skilled in the art, e.g. by freeze-drying.

The use of the terms "a" and "an" and "the" and similar referents in the context of describing the invention (especially in the context of the following claims) are to be construed to cover both the singular and the plural, unless otherwise Indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All values defined herein should be interpreted as "about" values, for example "2.0 M" should be understood as "about 2.0 M".

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

EXPERIMENTAL

Ex 1

Obtaining a Solution of Teicoplanin in Water

Ex 1a

A fermentation broth containing Teicoplanin is obtained by fermenting a culture of *A. Teichomyceticus* in a manner known per se, e.g. as disclosed in U.S. Pat. No. 4,239,751.

5 L teicoplanin containing whole culture fermentation broth from a laboratory fermentor was adjusted to pH 9.5 (by addition of 1M NaOH) and brought under stirring. The solution was filtered through a 100 μm depth filter (Polygrad, Millipore) at room temperature, following by ultra-filtration (500 000 Da, Biomax, Millipore) at 12-14 degrees Celsius. Residual Teicoplanin was recovered by diafiltration of the biomass in batch mode with 4*0.5 L water. About 80% of the teicoplanin present in the fermentation broth was recovered In the Final clarified solution.

Ex 1b 500 ml teicoplanin fermentation broth obtained as in ex 1a was adjusted to pH 9.5 with 1M NaOH and a cell free solution was achieved by centrifugation in a laboratory centrifuge at 10 degree celcius. About 85% of the teicoplanin present in the fermentation broth was recovered in the final clarified solution.

Ex 2

Ion Exchange Chromatography Purification

Ex 2a

Anion Exchange Chromatography Purification of Teicoplanin Factor A2 (TA2)

Clarified teicoplanin solution from ex 1a containing 0.5 g product was adjusted to pH 8 by addition of 1M HCl. NaCl was added to a final concentration of 0.5M, giving a conductivity of ca. 50 mS/cm. The methacrylate co-polymer anion exchange resin Macro-prep High Q support (Bio Rad) was packed into a chromatography column (inner diameter (i.d.) 1.6 cm, bed height 12 cm, volume 24 ml), and the prepared teicoplanin solution was added to the column at a flow rate of 3.4 ml/min. The column was washed with 48 ml 0.5M NaCl solution before eluting the product with 192 ml 3M acetic acid. 0.42 g teicoplanin was recovered in the elution pool, and the HPLC purity of the same pool did increase from about 70 area % to 90 area % TA2 by the operation, together with removal of a substantial amount of colored components.

Optionally a wash step comprising high NaCl concentration (i.e. up to 2M) was included In the chromatography process giving even higher purity and less color of the final product pool, with only minor loss of teicoplanin.

Ex 2b

Anion Exchange Chromatography Purification of TA2

Clarified teicoplanin solution from ex 1a containing 0.5 g product was adjusted to pH 8 by addition of 1M HCl. NaCl was added to a final concentration of 0.5M, giving a conductivity of ca. 50 mS/cm. The agarose based anion exchange resin Q Sepharose Fast Flow (Amersham Biosciences) was packed into a chromatography column (inner diameter (i.d.) 1.6 cm, bed height 12 cm, volume 24 ml), and the prepared teicoplanin solution was added to the column at a flow rate of 3.4 ml/min. The column was washed with 48 ml 0.5M NaCl-solution before eluting the product with 192 ml 3M acetic acid. 0.35 g teicoplanin was recovered in the elution pool, and the HPLC purity of the same pool did increase to approximately 85 area % TA2.

Ex 2c

Anion Exchange Chromatography for Purification of TA2

$NaHCO_3$ is added to a concentration of 0.7M in clarified teicoplanin solution from ex 1a containing 0.5 g product, and the pH of the solution is adjusted to pH 8 by addition of 1M HCl. The solution is thereafter applied to a column as described in example 2b. The column is washed with 48 ml 0.7M $NaHCO_3$-solution and eluted with 192 ml 3M acetic acid. Purified teicoplanin is recovered in the elution pool.

Ex 2d

Anion Exchange Chromatography for Purification of Vancomycin

A crude fermentation broth containing vancomycin can be produced according to the procedure of U.S. Pat. No. 5,223, 413, and clarified by centrifugation. NaCl is added to clarified vancomycin solution, containing 0.5 g product, to a concentration of 0.5M and the pH of the solution is adjusted to pH 10 (by 1M NaOH). The vancomycin solution is thereafter applied to a column as described in example 2a. The column is washed with 48 ml 0.5M NaCl-solution followed by elution of target with 192 ml 0.5M acetic acid. Purified vancomycin is recovered in the elution pool.

Ex 2e

Cation Exchange Chromatography

Clarified teicoplanin solution from ex 1a containing 0.5 g product is adjusted to pH 2.8 by addition of 1M HCl. NaCl is added to a final concentration of 0.3M NaCl. The solution is applied to a column (i.d. 1.6 cm, bed height 12 cm, volume 24 ml) packed with a methacrylate co-polymer cation exchange resin, i.e. Macro-prep High S support (Bio Rad). The column is washed with 48 ml 0.3M NaCl-solution followed by elution of target with 192 ml 0.2M sodium acetate at pH 6.0. Purified teicoplanin is recovered in the elution pool.

Ex 3

Teicoplanin was produced by fermentation and clarified as described in example 1a. Equal amounts of clarified broth containing 1.0 g teicoplanin were mixed with different amounts of NaCl (see table 1 below) to give from 0 to 1M NaCl in the solution. After dissolution, the samples were applied to a column as described in example 2a at a flow rate of 3.4 ml/min. The column was washed with 48 ml NaCl-solution with the equal molarity as in the applisate following elution of target with 192 ml 3M acetic acid. The binding capacity for teicoplanin and the HPLC purity were assayed by a standard HPLC method. The pool was selected such that the area % TA2 was about 90%.

The results are summarized in table 1 below:

TABLE 1

| NaCl concentration | Binding capacity [mg target/ml resin] | Relative colour content AU450/(g TA2/L) (elution pool) |
|---|---|---|
| 0.00M | 36 | 0.71 |
| 0.20M | 28 | 0.37 |
| 0.30M | 29 | 0.45 |
| 0.40M | 27 | 0.25* |
| 0.50M | 21 | 0.18 |
| 0.70M | 17 | 0.18 |
| 1.00M | 10 | 0.12 |

*value of 0.34 also obtained and value of 0.36 obtained employing 0.5 g product in place of 1.0 g Teicoplanin

Ex 4

Further Purification

The clarified (e.g. filtered or centrifuged) fermentation broth can be purified before applying the ion exchange step, and/or the solution from the ion exchange step can be further purified by applying one or more purification methods, such as method known per se or as described below:

Ex. 4a

Prepurification of Teicoplanin Before Anion Exchange—Loading to a Hydrophobic Backbone Clarified teicoplanin solution from ex 1a containing 0.5 g product is adjusted to pH 8 by addition of 1M HCl, and is applied to a column packed with a macroreticular aliphatic crosslinked polymer (XAD7HP, Rohm & Haas) (inner diameter (i.d.) 1.6 cm, height 10 cm, volume 20 ml) at a flow rate of 0.7 ml/min. After binding, the column is washed with 80 ml of water, before teicoplanin is recovered by elution with 100 ml of a 50/50 mixture of ethanol and water. The resulting eluate is committed to evaporation using a rotary evaporator unit, at 40 degree Celsius, 80 mbar. The resultant ethanol-free solution is treated as described in example 2a.

Ex 4b

Further Purification of TA2 in the Ion Exchange Pool by Loading to a Hydrophobic Interaction Resin A column with diameter 1.6 cm and a bed height of 10 cm (volume 20 ml) is packed with a hydrophobic interaction resin, i.e. Octyl Sepharose Fast Flow (Amersham Biosciences). The elution pool from example 2a is added ammonium sulfate to a concentration of 0.1M, and loaded to the column at pH 2.5 and a flow rate of 2.5 ml/min. The column is washed with 40 ml 0.1M ammonium sulfate solution and eluted by 120 ml water. Purified and less colored teicoplanin solution is recovered in the operation.

Ex. 4c

Further Purification of TA2 in the Ion Exchange Pool by Loading to a Cation Exchange Resin Product from one of the examples 2a-2c containing 0.35-0.45 g teicoplanin in acetic acid solution at pH 2.5 is applied to a cation exchange resin (Macro-prep High S support (Bio Rad), inner diameter 1.6 cm, height 10 cm, volume 20 ml) at a flow of 2.5 ml/min. The column is washed with 40 ml 0.1M acetic acid solution, followed by elution of target with 120 ml 0.2 M sodium acetate at pH 6.0. Purified teicoplanin is recovered in the elution pool.

Ex. 4d

Decolorization of TA2 in the Ion Exchange Pool by Carbon Filtration

The elution pool collected In example 2a was added 75 ml ethanol to a 50/50 vol % mixture before filtering through an immobilized active carbon filter (millistak+, 13 $cm^2$ filter area, Millipore). The filter was rinsed with 25 ml 50/50 vol % water/ethanol mixture. Teicoplanin was recovered in the almost color free product solution.

Ex. 4e

Decolorization of TA2 in the Ion Exchange Pool by Size Exclusion Chromatography 10 ml of the elution pool from example 2a is loaded to a 30 ml size exclusion column (Superdex 30 prepgrade, Amersham Biosciences) at a flow rate of 1 ml/min. Colored components in the sample that are larger than teicoplanin is eluted In front of teicoplanin and is thereby removed.

Ex. 4f

Precipitation of TA2 in the Ion Exchange Pool by Addition of an Organic Solvent

Teicoplanin in the elution pool from example 2a is precipitated from the solution by addition of 1370 ml acetone to a final concentration of 95%. The precipitate is harvested by filtration and the subsequent filter cake is washed twice with 10 ml acetone. The filter cake is thereafter dried in a vacuum oven at 40 degrees Celsius. Purified teicoplanin is recovered in the dry filter cake.

Preferred embodiments of this invention are described herein, including the best mode known to the inventors for carrying out the invention. Variations of those preferred embodiments may become apparent to those of ordinary skill in the art upon reading the foregoing description. The skilled artisan is able to upscale the methods disclosed herein. The inventors expect skilled artisans to employ such variations as appropriate, and the Inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Each of the above-mentioned patent documents and scientific articles are incorporated herein in their entirety by reference.

The invention claimed is:

1. A method for purification of a glycopeptide antibiotic using ion exchange chromatography, which comprises:
   a) adjusting the salt concentration in a solution of the glycopeptide antibiotic to at least 0.2 M, and/or adjusting the conductivity of the solution of the glycopeptide antibiotic to at least 20 mS/cm;
   b) contacting the solution of the glycopeptide antibiotic with an ion exchange material;
   c) optionally washing the ion exchange material; and
   d) removing the glycopeptide antibiotic from the ion exchange material, using an eluent.

2. The method of claim 1, wherein the conductivity of the solution of the glycopeptide is adjusted to above 20 mS/cm.

3. The method of claim 1, wherein the glycopeptide antibiotic is selected from the group consisting of a dalbaheptide, a group I vancomycin type glycopeptide; a group II avoparcin type glycopeptide; a group III ristocetin type glycopeptide; a group IV teicoplanin type glycopeptide; and a combination of one or more of the foregoing glycopeptide antibiotics.

4. The method of claim 1, wherein the glycopeptide antibiotic is selected from the group consisting of Teicoplanin; and Vancomycin.

5. The method of claim 1, wherein the ion exchange material is an anion exchange resin.

6. The method of claim 1, wherein the conductivity of the solution of the glycopeptide is above 30 mS/cm.

7. The method of claim 1, wherein the salt concentration during the ion exchange is higher than about 0.3 M.

8. The method of claim 1, wherein the salt concentration during the ion exchange is lower than about 1.5 M.

9. The method of claim 1, wherein an alkali metal salt is used for adjusting the salt concentration and/or the conductivity of the solution.

10. The method of claim 1, in which the eluent is an acid or a solution of a salt.

11. The method of claim 1, in which the eluent is an acid selected from the group consisting of a weak organic acid and a buffer comprising a weak organic acid and a corresponding base.

12. The method of claim 1, wherein the glycopeptide antibiotic is teicoplainin A2, and the method further comprises adding an organic solvent to the teicoplainin factor A2 in an eluate from step d) to precipitate the teicoplainin factor A2.

13. The method of claim 12, wherein the solution is colourless.

14. The method of claim 5, wherein the anion exchange resin has a polymeric hydrophilic backbone.

15. The method of claim 9, wherein the alkali metal salt is sodium, potassium or lithium salts of one of the following anions: $Cl^-$, $HSO_3^-$, $BrO_3^-$, $Br^-$, $NO_3^-$, $ClO_3^-$, $HSO_4^-$, $HCO_3^-$, $IO_3^-$, $HPO_4^{2-}$, formate, acetate, or propionate.

16. The method of claim 9, wherein the alkali metal salt is NaCl.

17. The method of claim 11, wherein the acid is acetic acid or citric acid.

18. The method of claim 11, wherein the buffer is below pH 4.5 and wherein the concentration of the weak organic acid eluent acid is in the range from 0.1 M to 6.0 M.

19. The method of claim 11, wherein the glycopeptide antibiotic is teicoplainin or vancomycin.

* * * * *